(12) United States Patent
Doherty

(10) Patent No.: US 6,544,983 B2
(45) Date of Patent: Apr. 8, 2003

(54) DIAZEPINOINDOLES FOR THE TREATMENT OF CHRONIC OBSTRUCTIVE PULMONARY DISEASE

(75) Inventor: Annette Doherty, Chatenay-Malabry (FR)

(73) Assignee: Pfizer Inc, New York, NY (US)

( * ) Notice: Subject to any disclaimer, the term of this patent is extended or adjusted under 35 U.S.C. 154(b) by 19 days.

(21) Appl. No.: 09/876,719

(22) Filed: Jun. 7, 2001

(65) Prior Publication Data

US 2002/0010175 A1 Jan. 24, 2002

(30) Foreign Application Priority Data

Jun. 9, 2000  (EP) .............................................. 00401646

(51) Int. Cl.$^7$ ............................................. A61K 31/55
(52) U.S. Cl. ..................................................... 514/220
(58) Field of Search ......................................... 514/220

(56) References Cited

U.S. PATENT DOCUMENTS

| | | | |
|---|---|---|---|
| 5,082,937 A | 1/1992 | Calvet et al. | |
| 5,852,190 A | 12/1998 | Pascal et al. | |
| 5,972,927 A | 10/1999 | Pascal et al. | ............... 514/211 |
| 6,239,130 B1 | 5/2001 | Pascal et al. | |

FOREIGN PATENT DOCUMENTS

WO    WO 97/36905    * 10/1997

OTHER PUBLICATIONS

Doherty, "Phosphodiesterase 4 inhibitors as novel anti-inflammatory agents", *Current Opinion in Chemical Biology*, vol. 3, 1999, pp 466–473.

Mohammed and Young, "Clinical aspects and treatment of chronic obstructive pulmonary disease", *Current Opinion in Anti-inflammatory & Immunomodulatory Investigational Drugs*, vol. 1, No. 1, 1999, pp 21–28.

Schmidt et al., "Selective phosphodiesterase inhibitors for the treatment of bronchial asthma and chronic obstructive pulmonary disease", *Clinical and Experimental Allergy*, vol. 29, Supplement 2, 1999, pp 99–109.

Nieman et al., "SB 207499 (Ariflo™), A Second–Generation, Selective Oral Phosphodiesterase Type 4 (PDE4) Inhibitor, Attenuates Exercise Induced Bronchoconstriction in Patients With Asthma", *Am. J. Respir. Crit. Care Med.*, vol. 157, No. 3, 1998, p A413.

Underwood et al., "The Second Generation Phosphodiesterase (PDE)4 Inhibitor, SB 207499, Inhibits Antigen–Induced Bronchoconstriction and Eosinophilia and LPS–Induced Airway Neutrophilia and Edema in the Guinea Pig", *Eur. Respir. J.*, vol. 12, Suppl. 29, 1998, p 86s.

Compton et al., "Ariflo™(SB 207499), A Second Generation, Oral PDE4 Inhibitor, Improves Quality of Life in Patients with COPD", *Am. J. Respir. Crit. Care Med.*, vol. 159, No. 3, 1999, p A522.

Murdoch et al., "The Safety and Tolerability of Ariflo™(SB 207499), A Novel & Selective Phosphodiesterase 4 Inhibitor, in Healthy Male Volunteers", *Am. J. Respir. Crit. Care Med.*, vol. 157, No. 3, 1998, p A409.

Burnouf et al., "Synthesis Structure–Activity Relationships, and Pharmacological Profile of 9–Amino–4–oxo–1–phenyl–3,4,6,7–tetrahydro[1,4]diazepino[6,7,1–hi]indoles: Discovery of Potent, Selective Phosphodiesterase Type 4 Inhibitors", *J. Med. Chem.*, vol. 43, No. 25, 2000, pp 4850–4867.

Barnes, "Chronic obstructive pulmonary disease: new opportunities for drug development", *TIPS*, vol. 19, 1998, pp 415–423.

Leckie et al., "Novel therapy for COPD", *Expert Opinion on Investigational Drugs*, vol. 9, No. 1, 2000, pp 3–23.

Pruniaox, "Novel Generation Phosphodiesterase 4 Inhibitors for the Treatment of Asthma"PDE Inhibitors: Drugs with an expanding range of therapeutic uses (Nice, France), William Harvey Research Conference Abstract, vol. 21, p. 20 (1999).

* cited by examiner

*Primary Examiner*—Raymond Henley, III
(74) *Attorney, Agent, or Firm*—Peter C. Richardson; Gregg C. Benson; Robert T. Ronau

(57) ABSTRACT

The present invention relates to the use of diazepinoindoles of the formula (I):

(I)

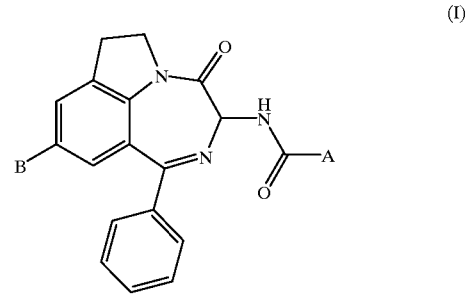

in which A is aryl or nitrogen-containing heteroaryl, and B is a hydroxyl or amino radical, for the treatment of chronic obstructive pulmonary disease.

15 Claims, 1 Drawing Sheet

DIAZEPINOINDOLES FOR THE TREATMENT OF CHRONIC OBSTRUCTIVE PULMONARY DISEASE

FIELD OF THE INVENTION

The present invention relates to the use of diazepinoindoles for the treatment of chronic obstructive pulmonary disease (hereinafter COPD).

TECHNICAL BACKGROUND OF THE INVENTION

COPD is a chronic, slowly progressive disorder characterized by airflow obstruction (associated with airways inflammation and an important neutrophil content). Most of the lung function impairment is fixed (although some reversibility can be produced by bronchodilator therapy). This disease will be referred to as COPD, although a number of clinical terms have been used in the past, either alone or in combination. These terms include emphysema, chronic bronchitis, chronic airflow limitation, chronic airways obstruction, non-reversible obstructive airways disease, chronic obstructive airways disease and chronic obstructive lung disease.

The clinical presentation of COPD can vary in severity from simple chronic bronchitis without disability to the severely disabled state with chronic respiratory failure. The major clinical features of patients suffering from COPD are chronic bronchitis and/or emphysema (associated with airways inflammation and/or an important neutrophil content).

Although the known prevalence of COPD is not complete, it can be ascertained that COPD is the fourth leading cause of death in developed countries, especially in the USA. Also, the problem of COPD is expected to grow, both in the developed western countries and in other countries in the coming years. A 3-fold increase is predicted to occur in the next ten years in the East Asia countries, as a large proportion of the male population is smoking.

Thus, there is a need for an efficient treatment of COPD.

In the past years, second-generation selective phosphodiesterase 4 inhibitors (PDE4 inhibitors) have been proposed as a potentially efficient treatment in COPD. See inter alia Doherty, *Current Opinion in Chemical Biology* 1999, 3:466–473; Mohammed et al, *Anti-inflammatory & Immunomodulatory Investigational* Drugs 1999 1(1):21–28; Schmidt et al., *Clinical and Experimental Allergy*, 29, supplement 2, 99–109.

Cilomilast (Ariflo®), an orally active PDE4 inhibitor, has been proposed as a treatment for COPD. See inter alia: Nieman et al, *Am J Respir Crit Care Med* 1998, 157:A413; Underwood et al, *Eur Respir J* 1998, 12:86s; Compton et al, *Am J Respir Crit Care Med* 1999, 159:A522. See also the oral presentations at the European Respiratory Society Meeting, Madrid, Oct. 12, 1999, by Compton, and at the 4$^{th}$ World Congress on Inflammation, Paris, Jun. 27–30, 1999, by Torphy and Underwood. This compound is currently in phase III clinical trials for COPD.

However, the use of cilomilast for treating COPD presents some drawbacks. It has been reported that when cilomilast is given at a single dose of 20 mg, relevant side effects such as nausea and vomiting occurred. See Murdoch et al, *Am J Respir Crit Care Med* 1998, 157:A409. Side effects appearing at such low dose will limit the application of cilomilast and will prevent daily single dosage forms, thus leading to patient discomfort.

SUMMARY OF THE INVENTION

The present invention proposes the use of a certain class of diazepinoindoles known as PDE4 inhibitors for the treatment of COPD. These compounds are devoid of adverse side effects, notably on the heart or digestive system (see Burnouf et al, *Journal of medicinal chemistry* (2000), 43:4850–4867), and are more efficient than cilomilast at lower doses.

The invention relates to the use of [1,4]diazepino[6,7,1-hi]indoles of formula (I)

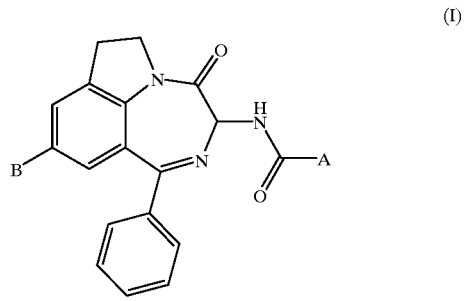

(I)

in which:

A is aryl or nitrogen-containing heteroaryl, each optionally being substituted with one to three groups chosen independently from halogen, lower alkyl, lower haloalkyl, lower alkoxy, cycloalkyloxy, amino and lower alkylcarbonyl-amino or alkyloxycarbonylamino;

B is a hydroxyl or amino radical, itself optionally substituted, or a pharmaceutically acceptable salt thereof, for the manufacture of a medicament for the treatment of chronic obstructive pulmonary disease or COPD.

The invention also provides a method for the treatment of COPD comprising administering to a human in need thereof an effective amount of a diazepinoindole of formula I.

These compounds, their use as PDE4 inhibitors and their preparation processes are disclosed in WO 97/36905, the content of which is incorporated herein by reference. These diazepinoindoles will be used in the invention as the active ingredient.

BRIEF DESCRIPTION OF THE DRAWINGS

The invention is disclosed in more details in the following specification, and in reference to the drawings, in which.

DETAILED DESCRIPTION OF THE INVENTION

Figure 1:
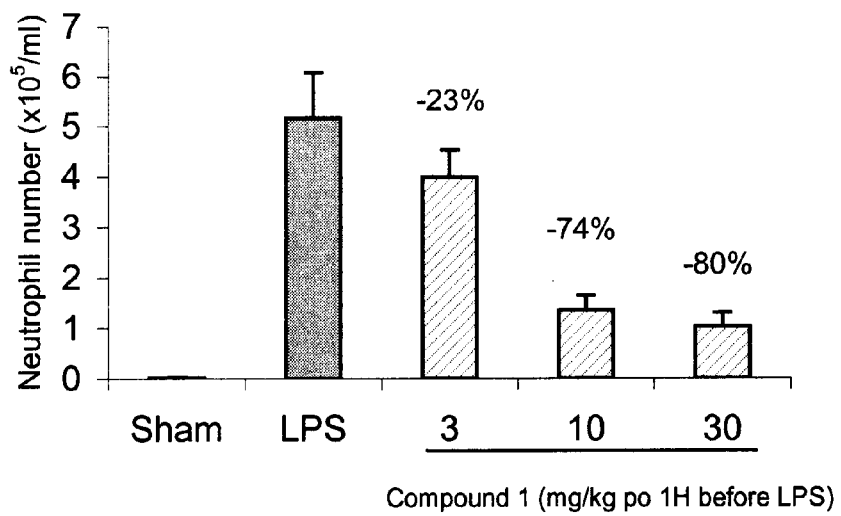
FIG. 1 shows the neutrophil count in the airways and the percentage of inhibition of the LPS-induced lung neutrophilia as a function of the amount of (3R)N-(9-amino-4-oxo-1-phenyl-3,4,6,7-tetrahydro-[1,4]diazepino[6,7,1-hi]indol-3-yl)-nicotinamide administered in Wistar rats.

The invention is particularly directed to the use of [1,4]diazepino[6,7,1-hi]indoles of the following formula (I)

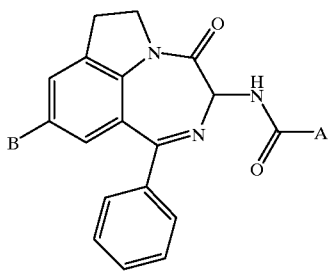

(I)

in which:
- A is aryl or nitrogen-containing heteroaryl, each optionally being substituted with one to three groups chosen independently from halogen, lower alkyl, lower haloalkyl, lower alkoxy, cycloalkyloxy, amino and lower alkylcarbonyl-amino or alkyloxycarbonylamino;
- B is:
  1) —OR$_1$, R$_1$ being —H or R$_4$,
  2) —NR$_2$R$_3$, R$_2$ being —C(NH)NH$_2$ and R$_3$ being —H,
  3) —NR$_2$R$_3$, R$_2$ being R$_4$ and R$_3$ being —H,
  4) —NR$_2$R$_3$, R$_2$ and R$_3$ independently being —H or lower alkyl, or
  5) —NR$_2$R$_3$, R$_2$ and R$_3$ forming, together with the nitrogen atom to which they are attached, a saturated five- to seven-membered heterocycle which may comprise, as second hetero atom not attached directly to the nitrogen atom, an oxygen, a sulfur or a nitrogen;
- R$_4$ is:
  1) —CH$_2$—CO$_2$H,
  2) —CO—(CH$_2$)$_p$—CO$_2$H,
  3) —CO—A, where A has the definition indicated above,
  4) —CO—CH=CH—CO$_2$H,
  5) —CO—(CH$_2$)$_n$—CH$_3$, n being an integer equal to or greater than 0 and less than or equal to 18,
  6) —CO—(CH$_2$—O—CH$_2$)$_p$—CH$_2$—O—CH$_3$,
  7) —CO—(CH$_2$—O—CH$_2$)$_p$—CO$_2$H,
  8) —(CH$_2$)$_p$—NR$_5$R$_6$, R$_5$ and R$_6$ independently being —H or lower alkyl, or
  9) —(CH$_2$)$_p$—NR$_5$R$_6$, R$_5$ and R$_6$ forming, together with the nitrogen atom to which they are attached, a saturated five- to seven-membered heterocycle which may comprise, as second heteroatom not attached directly to the nitrogen atom, an oxygen, a sulfur or a nitrogen;
- p is an integer equal to 2, 3 or 4;
- the racemic forms and isomers thereof, in particular those of configuration determined by carbon 3 of the diazepinoindol-4-one ring,
- as well as the pharmaceutically acceptable derivatives thereof, for the treatment of COPD.

A group of compounds (I) in which B is OR$_1$ or NR$_2$R$_3$ with R$_1$, R$_2$ and R$_3$ representing hydrogen is preferred.

Another set of products (I) consisting of those in which A is aryl substituted with 1 to 3 groups independently chosen from halogen, amino, lower alkyloxycarbonylamino or alkoxy is advantageously preferred, as well as the set of products (I) in which A is monocyclic heteroaryl comprising from 1 to 2 nitrogen atoms or bicyclic heteroaryl comprising from 1 to 4 nitrogen atoms.

More specifically, a group of compounds which has been found to be of particular interest for use in COPD include those compounds of formula I in which B is NH$_2$ and A is aryl substituted with 1 to 3 groups independently chosen from halogen and amino or monocyclic heteroaryl comprising from 1 to 2 nitrogen atoms.

In the following and in the foregoing text:
- aryl is understood to refer to phenyl or naphthyl;
- nitrogen-containing heteroaryl is understood to refer to a non-saturated monocycle or polycycle containing at least one nitrogen atom and, preferably, five- to seven-membered heteromonocycles containing from 1 to 4 nitrogen atoms, or alternatively non-saturated condensed heterocycles containing from 1 to 4 nitrogen atoms, optionally methylated or ethylated on a positively charged nitrogen atom;
- halogen is understood to refer to fluorine, chlorine, bromine or iodine;
- as regards radicals comprising an alkyl sequence, lower is understood to mean that the alkyl is linear or branched and contains from one to four carbon atoms, or alternatively represents the cyclopropylmethyl radical;
- cycloalkyl is understood to refer to cyclopropyl, cyclobutyl, cyclopentyl or cyclohexyl groups;
- haloalkyl is understood to refer to a mono-, di- or trihaloalkyl.

The compounds utilized in the invention include solvates, hydrates, pharmaceutically acceptable salts, and polymorphs (different crystalline lattice descriptors) of the compound of Formula I, which are pharmaceutically acceptable derivatives thereof.

The expression pharmacologically acceptable salt of a compound of formula (I) having a basic part should be understood to refer to the addition salts of the compounds of formula (I) which may be formed from non-toxic inorganic or organic acids such as, for example, hydrobromic, hydrochloric, sulfuric, phosphoric, nitric, acetic, succinic, tartaric, citric, maleic, hydroxymaleic, benzoic, fumaric, toluenesulfonic and isethionic acid salts, and the like. The various quaternary ammonium salts of the derivatives (I) are also included in this category of compounds of the invention. In addition, the expression pharmacologically acceptable salt of a compound of formula (I) having an acidic part is understood to refer to the usual salts of the compounds of formula (I) which may be formed from non-toxic inorganic or organic bases such as, for example, the hydroxides of alkali metals and alkaline-earth metals (sodium, potassium, magnesium and calcium), amines (dibenzylethylenediamine, trimethylamine, piperidine, pyrrolidine, benzylamine and the like) or alternatively quaternary ammonium hydroxides such as tetramethylammonium hydroxide. (See also "Pharmaceutical salts" by Berge S. M. et al. (1997) *J. Pharm. Sci.* 66: 1–19, which is incorporated herein by reference.).

Use of a prodrug of a compound of formula (I), such as would occur to one skilled in the art (see Bundgaard, et al., *Acta Pharm. Suec.,* 1987; 24: 233–246), is also contemplated.

The diazepinoindoles of formula (I) in which the asymmetric carbon atom in an alpha position relative to the "3-one" carbonyl of the diazepine ring possesses the (R) absolute configuration according to the Cahn-Ingold-Prelog rule are generally preferred.

More particularly, the following compounds of formula (I):
- (3R)-isoquinoline-3-carboxylic acid (9-hydroxy-4-oxo-1-phenyl-3,4,6,7-tetrahydro[1,4]diazepino[6,7,1-hi]indol-3-yl)amide;

(3R)-4-t-butyloxycarbonylamino-N-(9-amino-4-oxo-1-phenyl-3,4,6,7-tetrahydro[1,4]diazepino[6,7,1-hi]indol-3-yl)benzamide;

(3R)-4-amino-N-(9-amino-4-oxo-1-phenyl-3,4,6,7-tetrahydro[1,4]diazepino[6,7,1-hi]indol-3-yl)-3,5-dichlorobenzamide;

(3R)-4-amino-N-(9-amino-4-oxo-1-phenyl-3,4,6,7-tetrahydro[1,4]diazepino[6,7,1-hi]indol-3-yl)-5-chloro-2-methoxybenzamide;

(3R)-N-(9-amino-4-oxo-1-phenyl-3,4,6,7-tetrahydro-[1,4]diazepino[6,7,1-hi]indol-3-yl)isonicotinamide;

(3R)-3-t-butyloxycarbonylamino-N-(9-amino-4-oxo-1-phenyl-3,4,6,7-tetrahydro[1,4]diazepino[6,7,1-hi]indol-3-yl)isonicotinamide;

(3R)-isoquinoline-3-carboxylic acid (9-amino-4-oxo-1-phenyl-3,4,6,7-tetrahydro[1,4]diazepino[6,7,1-hi]indol-3-yl)amide;

(3R)-quinoline-3-carboxylic acid (9-amino-4-oxo-1-phenyl-3,4,6,7-tetrahydro[1,4]diazepino[6,7,1-hi]indol-3-yl)amide;

(3R)-4,7-dimethylpyrazolo[5,1-c][1,2,4]triazine-3-carboxylic acid (9-amino-4-oxo-1-phenyl-3,4,6,7-tetrahydro[1,4]diazepino[6,7,1-hi]indol-3-yl)amide;

(3R)-4-amino-3,5-dichloro-N-(9-dimethylamino-4-oxo-1-phenyl-3,4,6,7-tetrahydro[1,4]diazepino[6,7,1-hi]indol-3-yl)benzamide;

(3R)N-(9-amino-4-oxo-1-phenyl-3,4,6,7-tetrahydro-[1,4]diazepino[6,7,1-hi]indol-3-yl)-2-benzofuranecarboxamide;

(3R)4,7-dimethyl-pyrazolo[5,1-c][1,2,4]triazine-3-carboxylic acid[4-oxo-1-phenyl-9-(pyrrolidin-1-yl)-3,4,6,7-tetrahydro-[1,4]diazepino[6,7,1-hi]indol-3-yl]-amide;

pyridine-2-carboxylic acid (3R)-(9-amino-4-oxo-1-phenyl-3,4,6,7-tetrahydro-[1,4]diazepino[6,7,1-hi]indol-3-yl)amide pyrazine-2-carboxylic acid (3R)-(9-amino-4-oxo-1-phenyl-3,4,6,7-tetrahydro-[1,4]diazepino[6,7,1-hi]indol-3-yl)amide (3R)-4-amino-N-(9-amino-4-oxo-1-phenyl-3,4,6,7-tetrahydro-[1,4]diazepino[6,7,1-hi]indol-3-yl)benzamide; and (3R)N-(9-amino-4-oxo-1-phenyl-3,4,6,7-tetrahydro-[1,4]diazepino[6,7,1-hi]indol-3-yl)-nicotinamide are preferred for use for the manufacture of a medicament for the treatment of COPD.

Most preferred compounds are:

(3R)-4-amino-N-(9-amino-4-oxo-1-phenyl-3,4,6,7-tetrahydro-[1,4]diazepino[6,7,1-hi]indol-3-yl)-3,5-dichlorobenzamide;

(3R)-N-(9-Amino-4-oxo-1-phenyl-3,4,6,7-tetrahydro-[1,4]diazepino[6,7,1-hi]indol-3-yl)-isonicotinamide;

(3R)-N-(9-amino-4-oxo-1-phenyl-3,4,6,7-tetrahydro-[1,4]diazepino-[6,7,1-hi]indol-3-yl)nicotinamide; and (3R)-4-amino-N-(9-amino-4-oxo-1-phenyl-3,4,6,7-tetrahydro-[1,4]diazepino[6,7,1-hi]indol-3-yl)benzamide Especially preferred compounds of formula (I) are:

(3R)-4-amino-N-(9-amino-4-oxo-1-phenyl-3,4,6,7-tetrahydro-[1,4]diazepino[6,7,1-hi]indol-3-yl)benzamide (3R)N-(9-amino-4-oxo-1-phenyl-3,4,6,7-tetrahydro-[1,4]diazepino[6,7,1-hi]indol-3-yl)-nicotinamide (compound 1).

These compounds correspond to examples 11 and 3 of WO 97/36905.

The compounds used in the invention can be prepared according to the methods disclosed in WO 97/36905; the skilled person will refer to this document for the manufacture of the instant compounds.

The products of the invention are administered in the form of compositions, which are appropriate for the nature, and severity of the condition to be treated. The daily dose in humans can usually range from 2 mg to 1 g of product, which may be taken in one or more individual doses. The compositions are prepared in forms which are compatible with the intended route of administration, such as, for example, tablets, coated tablets, capsules, mouthwashes, aerosols, powders for inhalation, suppositories, gels or suspensions. These compositions are prepared by methods which are familiar to those skilled in the art and comprise from 0.5 to 60% by weight of active principle (compound of formula I) and 40 to 99.5% by weight of a pharmaceutical vehicle or carrier which is appropriate and compatible with the active principle and the physical form of the intended composition.

More particularly for the treatment of acute COPD conditions, the dosage form will generally be from about 20 mg to about 500 mg per day. Preferred doses will be from about 50 mg to about 300 mg per day (for an adult of 70 kg).

Preferably, the composition will be taken twice daily. More preferably, the composition will be taken once daily.

The frequency of administration is an important point for patient comfort when considering the treatment of chronic diseases such as COPD as these patients will be subjected to their treatment on a regular and long-term basis.

The elimination half-life of cilomilast (Torphy et al., Pulmonary Pharmacology & Therapeutics (1999) 12, 131–135) in humans is approximately 8 hours. Given this comparatively short half-life, a once daily administration of cilomilast for the treatment of COPD does not seem to be achievable: side effects appearing at doses of 20 mg preclude the use of high single doses; therefore a twice daily administration will be probably preferred.

The half-life of compound 1 has been determined in humans: single oral doses of compound 1, ranging from 1 to 25 mg, have been administered to healthy volunteers. Unexpectedly, mean terminal half-life values were similar at all doses, and comparatively long, ranging from 13.9 to 17.1 hours (mean: 15.4 hours). Such values indicate that compound 1 may be administered once daily.

By way of example, the composition and the preparation of tablets containing a compound of the invention are given below:

| Composition | Amount |
| --- | --- |
| Compound of formula (I) | 1 to 75 mg |
| Lactose | 124 to 74 mg |
| Microcrystalline cellulose | 36 to 60 mg |
| Polyvinylpyrrolidone | 6 mg |
| Sodium carboxymethyl starch | 8 mg |
| Magnesium stearate | 1 mg |

Mix together the active substance, the lactose, the microcrystalline cellulose and the carboxymethyl starch. Moisten and granulate using an aqueous or alcoholic polyvinylpyrrolidone solution of appropriate concentration. Dry and adjust the size distribution of the granule. Mix in the magnesium stearate homogeneously. Carry out tableting to give 200 mg per tablet.

Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid, which is in a mixture with the finely divided active component. In tablets, the active component is mixed with the carrier having the necessary binding properties in suitable proportions and compacted in the shape and size desired. For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify. The powders, tablets, cachets or encapsulated forms for capsules preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Tablets, powders, cachets, and capsules can be used as solid dosage forms suitable for oral administration. The drug may be delivered as a spray (either in a pressurised container fitted with an appropriate valve or in a non-pressurised container fitted with a metering valve).

Liquid form preparations include solutions, suspensions, and emulsions.

Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavouring agents, stabilisers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of drug. The unit dosage form can be a packaged preparation, the package containing discrete quantities of the preparation, for example, packaged tablets, capsules, and powders in vials or ampoules. The unit dosage form can also be a capsule, cachet, or tablet itself, or it can be the appropriate number of any of these packaged forms.

The following examples illustrate the invention without limiting it.

The model retained to assess the usefulness of the compounds of the invention for the treatment of COPD was a neutrophilia model. Neutrophilia was induced by exposure of rats or mice to a lipopolysaccharide (LPS) aerosol.

EXAMPLE 1

Neutrophilia Induced by LPS Aerosol in the C57 bl/6 Mouse 1.1 Experimental Protocol
Administration of Compound 1
The animals were treated with compound 1 when conscious, that was by the oral route.

Exposure to the LPS
One hour after treatment, the mice were placed in a plexiglass box (at most 25 mice to a box) and were given a 100 μg/ml aerosol of LPS (*Escherichia coli,* serotype O55:B5) for 1 hour. Control mice were not given the LPS aerosol.

Anaesthesia and Tracheotomy
Twenty-four hours after the exposure to the LPS, the animals were then anaesthetised by an intraperitoneal injection of 0.6% sodium pentobarbital at a rate of 15 ml/kg. A tracheotomy was carried out and a tracheal cannula was inserted.

Bronchoalveolar Washings
Using a 1 ml syringe, 6 consecutive washings were carried out with a 0.3 ml volume of a PBS solution (37° C.) in order to recover the cell population which was present in the lumen of the airways. The fluid which had thus been withdrawn was stored at +4° C. on ice.

Determination of the Cell Composition of the Bronchoalveolar Washings
The cells contained in the bronchoalveolar washing fluid were counted using a Coulter particle counter. Having been deposited on a microscope slide by centrifugation (Cytospin®), the samples were then stained with May Grunwald—Giemsa stain. The cell populations were differentiated under a microscope (×100) in accordance with morphological criteria.

Assessment Criterion
The main assessment criterion was the number of neutrophils/ml of bronchoalveolar washings. It was expressed in $10^5$ (E+05) cells/ml.

Expression of the Results
The arithmetic mean and the standard deviation (SD) of the number of neutrophils in the bronchoalveolar washing fluids were calculated for each treatment group. The percentage inhibition was calculated in the following manner:

$$(\text{percentage inhibition})_{Treated} = \frac{C_{Positive\ control} - C_{Treated}}{C_{Positive\ control}} \times 100$$

$C_{Positive\ co}$ntrol: Arithmetic mean of the cell concentration in the positive control group, with this value being taken as being the 0% inhibition.

$C_{Treated}$: Arithmetic mean of the cell concentration in the treated (or reference) group.

The 90% confidence interval for the percentage inhibition was to be calculated by the "Delta method" or "Fieller method" [i, ii & iii] (Armitage & al, 1998; Feuerstein & al, 1997; Hubert & al, 1988) if appropriate.

1.2 Results

Results of these experiments showed that compounds of formula I and particularly compound 1 strongly inhibited the LPS-induced lung neutrophilia in mice.

EXAMPLE 2

Neutrophilia Induced by LPS Aerosol in the Wistar Rat 2.1 Experimental Protocol
Administration of the Treatments
The animals were treated with compound 1 or cilomilast when conscious, that was by the oral route.

Exposure to the LPS
One hour after the treatment, the rats were placed in a plexiglass box and were given a 200 μg/ml aerosol of LPS (*Escherichia coli*, serotype O55:B5) for 1 hour. Control rats were not given the LPS aerosol. This control is called 'sham' in FIGS. 1 and 2.

Anaesthesia and Tracheotomy

Two hours after the exposure to the LPS, the animals were then anaesthetised by intraperitoneal injection of 6% sodium pentobarbital at a rate of 1 ml/kg. A tracheotomy was carried out and a tracheal cannula was inserted.

Bronchoalveolar Washings

Using a 5-ml syringe, 3 consecutive washings were carried out with a 5-ml volume of a 0.9% M NaCl+EDTA solution (37° C.), in order to recover the cell population present in the lumen of the airways. The fluid which had thus been withdrawn was stored at +4° C. on ice.

Determination of the Cell Composition of the Bronchoalveolar Washings

See Example 1.

Assessment Criterion

See Example 1.

Expression of the Results

See Example 1.

2.2 Results

Figure 2:
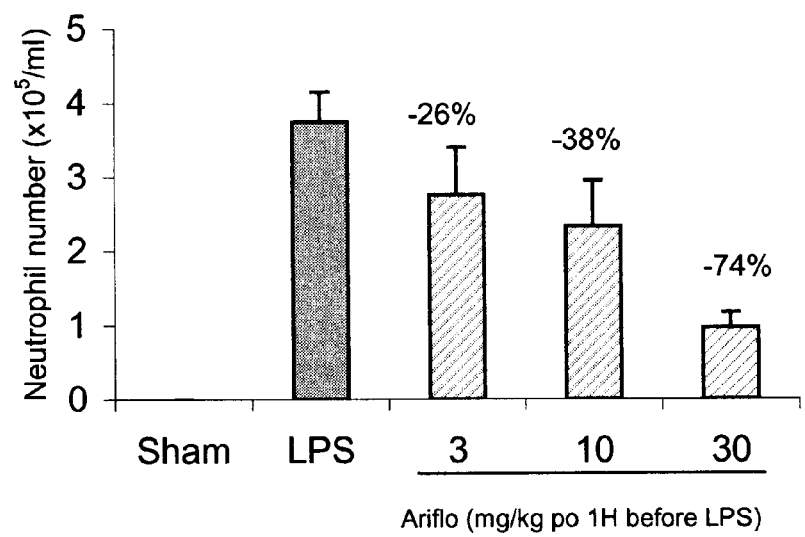
FIG. 2 shows the neutrophil count in the airways and the percentage of inhibition of the LPS-induced lung neutrophilia as a function of the amount of cilomilast (cis-4-cyano-4-[3-(cyclopentyloxy)-4-methoxyphenyl]cyclohexane carboxylic acid) administered in Wistar rats.

As indicated in FIG. 1, compound 1 strongly and significantly inhibits the LPS-induced lung neutrophilia in Wistar rats, with a percentage of inhibition of 74% at the dose of 10 mg/kg.

Comparison of these results with those obtained with cilomilast (Ariflo®) in the same model (FIG. 2) indicates that compound 1 (with a percentage of inhibition of 80% at 30 mg/kg) is more effective than cilomilast at that same dose. But especially at 10 mg/kg compound 1 is twice more efficient than cilomilast at the same dose. In other words, compound 1 is as active at 10 mg/kg (percentage of inhibition: 74%) as cilomilast at 30 mg/kg (percentage of inhibition: 74%).

EXAMPLE 3

Inhibition of In vitro LPS-induced $TNF_\alpha$ Production in Whole Blood of COPD Patients The aim of this study was to compare the in vitro activities of three selective PDE4 inhibitors (compound 1, rolipram which is 4-[3-(cyclopentyloxy)-4-methoxy-phenyl]-2-pyrrolidinone, and cilomilast) at reducing lipopolysaccharide (LPS)-induced $TNF_\alpha$ release in whole blood of COPD patients. Thirteen COPD patients, diagnosed according to the ATS guidelines[iv], were included in this study to determine the concentration-effect of LPS on $TNF^\alpha$ production (n=6) and the $IC_{50}$ values of compound 1, rolipram and cilomilast (n=7).

3.1 Experimental Protocol

Blood (15 ml/patient) was collected in heparin tubes and distributed in 96-well microplates (250 μl/well).

After a 30-min incubation at 37° C., 25 μl of increasing concentrations of the compound to test or vehicle were added in different wells. The microplates were incubated at 37° C. for 30 min, and then 25 μl of LPS (*E. coli*) at 50 μg/ml (stimulated wells) or 25 μl of sterile saline (unstimulated wells) were added. The microplates were incubated 22–24 h at 37° C.

125 μl of the supernatant plasma were transferred gently in sterile 96-well microplates and stored at −80° C. until $TNF_\alpha$ assay. The $TNF_\alpha$ production was then measured by an ELISA assay.

3.2 Results

After overnight incubation with LPS, whole blood $TNF_\alpha$ levels increased in a concentration-dependent manner from undetectable baseline levels to a mean of 8.1±2.0 ng/ml at 50 μg/ml LPS. Pre-incubation with compound 1 resulted in a dose-dependent inhibition of $TNF_\alpha$ release with an $IC_{50}$ value of 1.3±0.7 μM. The $IC_{50}$ values were 2.8±0.9 μM for rolipram and >10 μM for cilomilast. These data indicate that compound 1, which inhibits in vitro LPS-induced $TNF_\alpha$ release in COPD patients better than rolipram and cilomilast do, may be used as an anti-inflammatory therapy in this disease.

[i] ARMITAGE P. & COLTON T. (1998). Fieller's Theorem. Encyclopedia of Biostatistics, Volume 2, pp. 1515–1516. Wiley, N.Y.

[ii] FEUERSTEIN T. J., ROSSNER R. & SCHUMACHER M. (1997). How to Express an Effect Mean as Percentage of a Control Mean. Journal of Pharmacology and Toxicology Methods 37, pp. 187–190.

[iii] HUBERT J. J., BOHIDARD N. R. & PEACE K. E. (1988). Biopharmaceutical Statistics for Drug Development, Assessment of Pharmacological Activity section, pp. 83–148. Karl peace, N.Y.

[iv] Am. J. Respir. Crit. Care Med. 1995; 152: S77–S120.

What is claimed is:

1. A method for the treatment of COPD comprising administering to a human in need thereof an effective amount of a diazepinoindole of formula I,

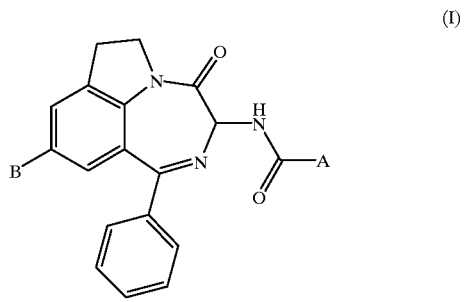

(I)

in which:

A is aryl or nitrogen-containing heteroaryl, each optionally being substituted with one to three groups chosen independently from halogen, lower alkyl, lower haloalkyl, lower alkoxy, cycloalkyloxy, amino and lower alkylcarbonylamino or alkyloxycarbonylamino;

B is:
1) —$OR_1$, $R_1$ being —H or $R_4$,
2) —$NR_2R_3$, $R_2$ being —C(NH)$NH_2$ and $R_3$ being —H,
3) —$NR_2R_3$, $R_2$ being $R_4$ and $R_3$ being —H,
4) —$NR_2R_3$, $R_2$ and $R_3$ independently being —H or lower alkyl, or
5) —$NR_2R_3$, $R_2$ and $R_3$ forming, together with the nitrogen atom to which they are attached, a saturated five- to seven-membered heterocycle which may comprise, as second hetero atom not attached directly to the nitrogen atom, an oxygen, a sulfur or a nitrogen;

R$_4$ is:

1) —CH$_2$—CO$_2$H,

2) —CO—(CH$_2$)$_p$—CO$_2$H,

3) —CO—A, where A has the definition indicated above,

4) —CO—CH═CH—CO$_2$H,

5) —CO—(CH$_2$)$_n$—CH$_3$, n being an integer equal to or greater than 0 and less than or equal to 18, 6) —CO—(CH$_2$—O—CH$_2$)$_p$—CH$_2$—O—CH$_3$, 7) —CO—(CH$_2$—O—CH$_2$)$_p$—CO$_2$H, 8) —(CH$_2$)$_p$—NR$_5$R$_6$, R$_5$ and R$_6$ independently being —H or lower alkyl, or 9) —(CH$_2$)$_p$—N—R$_5$—R$_6$, R$_5$ and R$_6$ forming, together with the nitrogen atom to which they are attached, a saturated five- to seven-membered heterocycle which may comprise, as second hetero atom not attached directly to the nitrogen atom, an oxygen, a sulfur or a nitrogen;

p is an integer equal to 2, 3 or 4;

the racemic forms and isomers thereof, as well as a pharmaceutically acceptable derivative thereof.

2. A method according to claim 1, characterized in that the diazepinoindole of formula (I) has an R absolute configuration according to the Cahn-Ingold-Prelog rule, considering the asymmetric carbon atom in an alpha position relative to the carbonyl of the diazepine ring.

3. A method according to claim 1 or 2, characterized in that in the diazepinoindole of formula (I), B is OR$_1$ or NR$_2$R$_3$ where R$_1$, R$_2$ and R$_3$ are hydrogen.

4. A method according to claim 1 or 2, characterized in that in the diazepinoindole of formula (I), A is aryl substituted with one to 3 groups independently chosen from halogen, amino, lower alkyloxycarbonylamino or alkoxy.

5. A method according to claim 3, characterized in that in the diazepinoindole of formula (I), A is aryl substituted with one to 3 groups independently chosen from halogen, amino, lower alkyloxycarbonylamino or alkoxy.

6. A method according to claim 1 or 2, characterized in that in the diazepinoindole of formula (I), A is monocyclic nitrogen-containing heteroaryl comprising from 1 to 2 nitrogen atoms or bicyclic nitrogen-containing heteroaryl comprising from 1 to 4 nitrogen atoms.

7. A method according to claim 3, characterized in that in the diazepinoindole of formula (I), A is monocyclic nitrogen-containing heteroaryl comprising from 1 to 2 nitrogen atoms or bicyclic nitrogen-containing heteroaryl comprising from 1 to 4 nitrogen atoms.

8. A method according to claim 6, characterized in that the heteroaryl is substituted with amino, lower alkyl, lower alkyloxycarbonylamino or alkylcarbonylamino groups.

9. A method for the treatment of COPD comprising administering to a human in need thereof an effective amount of a compound of formula (I),

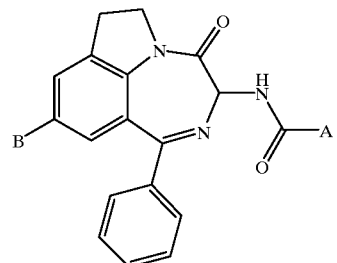

in which B is NH$_2$ and A is aryl substituted with 1 to 3 groups independently chosen from halogen and amino, as well as a pharmaceutically acceptable derivative thereof.

10. A method for the treatment of COPD comprising administering to a human in need thereof an effective amount of a compound of formula (I),

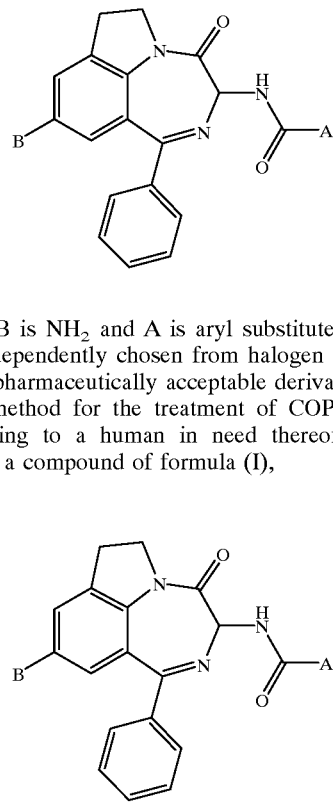

in which B is NH$_2$ and A is a monocyclic heteroaryl comprising from 1 to 2 nitrogen atoms, as well as a pharmaceutically acceptable derivative thereof.

11. A method for the treatment of COPD comprising administering to a human in need thereof an effective amount a compound selected from:

(3R)-isoquinoline-3-carboxylic acid (9-hydroxy-4-oxo-1-phenyl-3,4,6,7-tetrahydro[1,4]diazepino[6,7,1-hi]indol-3-yl)amide;

(3R)-4-t-butyloxycarbonylamino-N-(9-amino-4-oxo-1-phenyl-3,4,6,7-tetrahydro[1,4]diazepino[6,7,1-hi]indol-3-yl)benzamide;

(3R)-4-amino-N-(9-amino-4-oxo-1-phenyl-3,4,6,7-tetrahydro[1,4]diazepino[6,7,1-hi]indol-3-yl)-3,5-dichlorobenzamide;

(3R)-4-amino-N-(9-amino-4-oxo-1-phenyl-3,4,6,7-tetrahydro[1,4]diazepino[6,7,1-hi]indol-3-yl)-5-chloro-2-methoxybenzamide;

(3R)-N-(9-amino-4-oxo-1-phenyl-3,4,6,7-tetrahydro-[1,4]diazepino[6,7,1-hi]indol-3-yl)isonicotinamide (3R)-3-t-butyloxycarbonylamino-N-(9-amino-4-oxo-1-phenyl-3,4,6,7-tetrahydro[1,4]diazepino[6,7,1-hi]indol-3-yl)isonicotinamide;

(3R)-isoquinoline-3-carboxylic acid (9-amino-4-oxo-1-phenyl-3,4,6,7-tetrahydro[1,4]diazepino[6,7,1-hi]indol-3-yl)amide;

(3R)-quinoline-3-carboxylic acid (9-amino-4-oxo-1-phenyl-3,4,6,7-tetrahydro[1,4]diazepino[6,7,1-hi]indol-3-yl) amide;

(3R)-4,7-dimethylpyrazolo[5,1-c][1,2,4]triazine-3-carboxylic acid (9-amino-4-oxo-1-phenyl-3,4,6,7-tetrahydro[1,4]diazepino[6,7,1-hi]indol-3-yl)amide;

(3R)-4-amino-3,5-dichloro-N-(9-dimethylamino-4-oxo-1-phenyl-3,4,6,7-tetrahydro[1,4]diazepino[6,7,1-hi]indol-3-yl)benzamide;

(3R)N-(9-amino-4-oxo-1-phenyl-3,4,6,7-tetrahydro-[1,4]diazepino[6,7,1-hi]indol-3-yl)-2-benzofuranecarboxamide;

(3R)4,7-dimethyl-pyrazolo[5,1-c][1,2,4]triazine-3-carboxylic acid[4-oxo-1-phenyl-9-(pyrrolidin-1-yl)-3,4,6,7-tetrahydro-[1,4]diazepino[6,7,1-hi]indol-3-yl]-amide pyridine-2-carboxylic acid (3R)-(9-amino-4-oxo-1-phenyl-3,4,6,7-tetrahydro-[1,4]diazepino[6,7,1-hi]indol-3-yl)amide pyrazine-2-carboxylic acid (3R)-(9-amino-4-oxo-1-phenyl-3,4,6,7-tetrahydro-[1,4]diazepino[6,7,1-hi]indol-3-yl)amide (3R)-4-amino-N-(9-amino-4-oxo-1-phenyl-3,4,6,7-tetrahydro-[1,4]diazepino[6,7,1-hi]indol-3-yl)benzamide; or, (3R)N-(9-amino-4-oxo-1-phenyl-3,4,6,7-tetrahydro-[1,4]diazepino[6,7,1-hi]indol-3-yl)-nicotinamide, as well as a pharmaceutically acceptable derivative thereof.

12. A method for the treatment of COPD comprising administering to a human in need thereof an effective amount a compound selected from:

(3R)-4-amino-N-(9-amino-4-oxo-1-phenyl-3,4,6,7-tetrahydro-[1,4]diazepino[6,7,1-hi]indol-3-yl)-3,5-dichlorobenzamide;

(3R)-N-(9-Amino-4-oxo-1-phenyl-3,4,6,7-tetrahydro-[1,4]diazepino[6,7,1-hi]indol-3-yl)-isonicotinamide;

(3R)-N-(9-amino-4-oxo-1-phenyl-3,4,6,7-tetrahydro-[1,4]diazepino-[6,7,1-hi]indol-3-yl)nicotinamide; or, (3R)-4-amino-N-(9-amino-4-oxo-1-phenyl-3,4,6,7-tetrahydro-[1,4]diazepino[6,7,1-hi]indol-3-yl)benzamide, as well as a pharmaceutically acceptable derivative thereof.

13. A method for the treatment of COPD comprising administering to a human in need thereof an effective amount of (3R)-4-amino-N-(9-amino-4-oxo-1-phenyl-3,4,6,7-tetrahydro-[1,4]diazepino[6,7,1-hi]indol-3-yl)benzamide, as well as a pharmaceutically acceptable derivative thereof.

14. A method for the treatment of COPD comprising administering to a human in need thereof an effective amount of (3R)N-(9-amino-4-oxo-1-phenyl-3,4,6,7-tetrahydro-[1,4]diazepino[6,7,1-hi]indol-3-yl)-nicotinamide, as well as a pharmaceutically acceptable derivative thereof.

15. A method according to claim 1, wherein said racemic and isomers are those of configuration determined by carbon 3 of the diazepinoindol-4-one ring.

* * * * *